US010596092B2

(12) United States Patent
Lao

(10) Patent No.: US 10,596,092 B2
(45) Date of Patent: Mar. 24, 2020

(54) DEODORANT COMPOSITION AND A METHOD FOR PREPARING THEREOF

(71) Applicant: Chung Hing Lao, Kowloon (HK)

(72) Inventor: Chung Hing Lao, Kowloon (HK)

( * ) Notice: Subject to any disclaimer, the term of this patent is extended or adjusted under 35 U.S.C. 154(b) by 15 days.

(21) Appl. No.: 15/790,238

(22) Filed: Oct. 23, 2017

(65) Prior Publication Data

US 2019/0021975 A1    Jan. 24, 2019

(30) Foreign Application Priority Data

Jul. 24, 2017   (CN) .......................... 2017 1 0607267

(51) Int. Cl.

| A61K 8/49 | (2006.01) |
|---|---|
| A61K 8/19 | (2006.01) |
| A61Q 15/00 | (2006.01) |
| A61K 8/34 | (2006.01) |
| A61Q 17/00 | (2006.01) |

(52) U.S. Cl.
CPC .............. *A61K 8/4966* (2013.01); *A61K 8/19* (2013.01); *A61K 8/345* (2013.01); *A61Q 15/00* (2013.01); *A61Q 17/005* (2013.01)

(58) Field of Classification Search
CPC ................ A61K 8/41; A61K 2800/262; A61K 2800/31; A61K 2800/56; A61K 2800/77; A61K 8/0229; A61K 8/042; A61K 8/11; A61K 8/26; A61K 8/28; A61K 8/39; A61K 8/40; A61K 8/42; A61K 8/445; A61K 8/46; A61K 8/49; A61K 8/4913; A61K 8/4926; A61K 8/494; A61K 8/4946; A61K 8/496; A61K 8/498; A61K 8/4986; A61K 8/602; A61K 8/738; A61Q 15/00; A61Q 13/00; A61Q 19/00; A61Q 19/10; A61Q 5/02; A61L 9/01
See application file for complete search history.

(56) References Cited

U.S. PATENT DOCUMENTS

| 5,405,605 A   * | 4/1995 | Shin ..................... A61K 8/0229 |
|---|---|---|
| | | 424/66 |
| 2014/0170101 A1* | 6/2014 | Cetti ........................ A61K 8/46 |
| | | 424/65 |

FOREIGN PATENT DOCUMENTS

CN        100370985 C  *  2/2008  .......... A61K 31/445

OTHER PUBLICATIONS

CN100370985C, Juntang, Zhou inventor; Feb. 27, 2008; translation. (Year: 2008).*

* cited by examiner

*Primary Examiner* — Audrea B Coniglio

(57) ABSTRACT

The present invention relates to a composition and a deodorizing preparation comprising such composition for reducing, inhibiting or suppressing malodour developed from a body part of a subject. The composition comprises an active ingredient in an effective amount, the active ingredient comprising one or more of a hexamine, a derivative thereof and a compound thereof. The composition further comprises a buffer system adapted to maintain pH of the composition within a range of about 7.0 to about 11.0 when the composition is applied on the body part. The buffer system is adapted to substantially neutralise topical acidity of the body part to thereby reduce or minimise generation of skin-irritating formaldehyde from the hexamine comprising active ingredient.

13 Claims, 2 Drawing Sheets

DEODORANT COMPOSITION AND A METHOD FOR PREPARING THEREOF

FIELD OF THE INVENTION

The invention relates to a composition for use in a deodorant for a body part of a subject, and particularly, but not exclusively, to a deodorant preparation comprising a low- or reduced-skin irritating composition.

BACKGROUND OF THE INVENTION

Body odor generally refers to a condition in which an unpleasant smell or a malodor is released from a body part or skin of a body part of a human subject. Although body odor is known to be influenced by various physiological conditions, it is generally related to perspiration or sweating of the subject, and the subsequent bacterial decomposition of the organic compounds present in the sweat which forms the malodor carrying volatile organic acids. It is therefore most common for body odor to develop at axillary regions of the body such as the underarm areas where a large number of sweat glands are located, although body odor may also develop at other parts of the human body such as the palms of the hands, the soles of the feet, the upper thighs and the back region.

Various deodorant compositions and/or preparations have been developed to reduce, alleviate, eliminate or mask the unpleasant smell, and/or to suppress or inhibit the production of sweat from the skin of the body parts. In general, the deodorants may work by providing an antiseptic effect to inhibit the bacterial decomposition; by incorporating an anti-perspiring agent to suppress or inhibit perspiration; and/or by introducing fragrance to mask the generated odor. Deodorant preparations may come in different forms, such as solid, gel, cream, liquid or aerosol for various applications such as apply-on or roll-on sticks or rollers, body sprays or even body wipes; and can be classified as a cosmetic or a pharmaceutical product depending on the specific active ingredients in the composition. A number of commonly used deodorizing actives include alcohols, triclosan, sodium stearate, ethylenediaminetetraacetic acid (EDTA), chlorhexidine and formaldehyde, etc. for their antibacterial function; and/or salts of aluminum or zinc such as aluminum chloride, aluminum chlorohydrate, and aluminum-zirconium compound, etc. as antiperspirants. In addition to these commonly used actives, hexamine, which is also known as hexamethylenetetramine or methenamine, is found to be a potent deodorizing agent, although its deodorizing mechanism is yet to be clearly understood. Nevertheless, hexamine comprising deodorant preparations have also been reported to cause skin irritation to the users, which may potentially relate to the release of formaldehyde from hexamine in use.

OBJECTS OF THE INVENTION

An object of the present invention is to provide a novel composition for use in reducing, inhibiting or suppressing development of malodor from a body part of a human subject.

Another object of the present invention is to provide a low, or reduced, skin irritating composition for use in deodorant preparations.

A further object of the present invention is to mitigate or obviate to some degree one or more problems associated with known deodorant compositions and/or preparations, or at least to provide a useful alternative.

The above objects are met by the combination of features of the main claims; the sub-claims disclose further advantageous embodiments of the invention.

One skilled in the art will derive from the following description other objects of the invention. Therefore, the foregoing statements of object are not exhaustive and serve merely to illustrate some of the many objects of the present invention.

SUMMARY OF THE INVENTION

In general, the invention provides a composition for reducing, inhibiting or suppressing malodor developed from a body part of a subject, such as but not limited to, a human subject. Particularly, the invention provides a low, or reduced, skin irritating, hexamine comprising composition for use in a deodorant preparation which demonstrates high potency in reducing, inhibiting or suppressing development of sweat relating malodor via a multifunctional deodorizing mechanism.

In a first main aspect, the invention provides a composition for reducing, inhibiting or suppressing malodour developed from a body part of a subject. The composition comprises an active ingredient in an effective amount, with the active ingredient comprising one or more of a hexamine, a derivative thereof and a compound thereof. The composition further comprises a buffer system adapted to maintain pH of the composition within a range of about 7.0 to about 11.0 when the composition is applied on the body part.

In a second main aspect, the invention provides a deodorizing preparation for use at a body part of a subject. The deodorizing preparation comprises the composition of the first main aspect.

In a third main aspect, the invention provides a method of preparing a low skin-irritating composition for use in reducing, inhibiting or suppressing malodor from a body part of a subject. The method comprises providing an active ingredient in an effective amount, with the active ingredient comprising one or more of hexamine, a derivative thereof and a compound thereof; providing a buffer system adapted to maintain pH of the composition within a range of about 7.0 to about 11.0 when the composition is applied on the body part; wherein the buffer system is adapted to substantially neutralize topical acidity of the body part thereby reducing or minimizing generation of skin-irritating by-product from the active ingredient.

The summary of the invention does not necessarily disclose all the features essential for defining the invention; the invention may reside in a sub-combination of the disclosed features.

BRIEF DESCRIPTION OF THE DRAWINGS

The foregoing and further features of the present invention will be apparent from the following description of preferred embodiments which are provided by way of example only in connection with the accompanying figure, of which.

DESCRIPTION OF PREFERRED EMBODIMENTS

Figure 1:
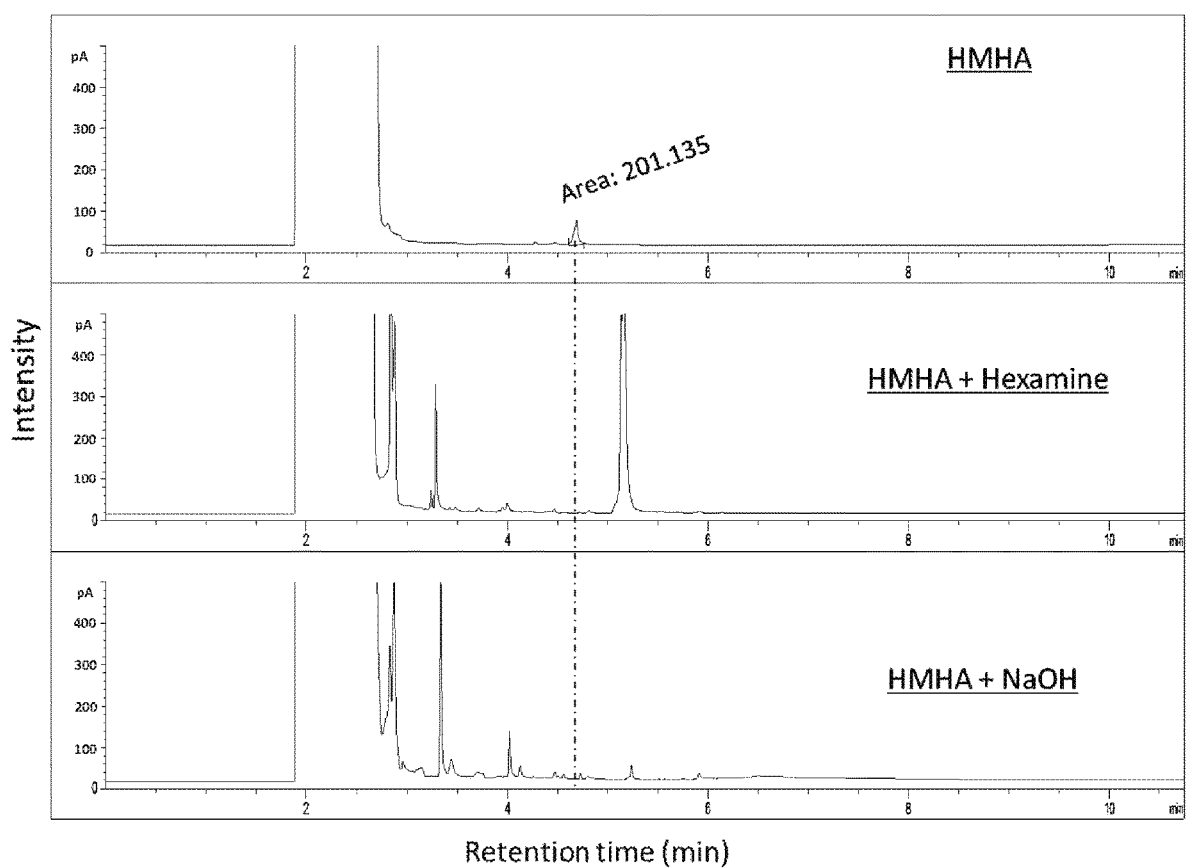
FIG. 1 is a Gas Chromatograph with a Flame Ionization Detector (GC-FID) chromatogram showing neutralization of 3-hydroxy-3-methyl-hexanoic acid (HMHA) by sodium hydroxide and hexamine.

The following description is of preferred embodiments by way of example only and without limitation to the combination of features necessary for carrying the invention into effect.

Reference in this specification to "one embodiment" or "an embodiment" means that a particular feature, agent, composition, preparation or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The present invention relates to a composition for reducing, inhibiting or suppressing malodor such as sweat relating malodor developed from a body part of a subject, such as an animal subject or a human subject. Particularly, the invention provides a low, or reduced, skin irritating, hexamine comprising composition for use in a deodorant preparation which is capable of demonstrating high potency in reducing, inhibiting or suppressing development of sweat relating malodor. The composition is generally applicable for use on any body parts such as axillary regions of the human body including underarm areas, where a large number of sweat glands are present. Nevertheless, a person skilled in the art would understand that the present invention shall not be limited to axilla applications, but also applicable to any other suitable body parts where sweating is likely to occur, which may include, but is not limited to, hands, feet, upper thighs and/or back region.

In the context of the present invention, the term "deodorant" relates in broad terms to encompass any agents, compositions, preparations, formulations and/or products adapted to reduce, inhibit, prevent, suppress, eliminate, mask odor, and more specifically, malodor; and that the "deodorizing" actions can be achieved by any known and possible mechanisms, such as but not limited to, the incorporation of antiperspirant, antibacterial agent, disinfectant or fragrance into the composition. The term "deodorant" in the context of the present invention therefore encompasses compositions and products in both cosmetic and pharmaceutical applications.

Hexamine, which is also known as hexamethylenetetramine or methenamine, has been traditionally used as a pharmaceutical active ingredient for controlling urinary tract infection by releasing formaldehyde and ammonia in acidic urine, with formaldehyde being a potent antibiotic that stops the growth of bacteria in the urinary track. Recently, increasing attention has been made to the use of hexamine as an active ingredient in deodorant formulations, although the relevant deodorizing mechanism is not yet clearly understood. One widely acceptable presumption is that hexamine, in the presence of sweat with a natural pH of about 4.0 to 7.0, releases formaldehyde which possesses antibacterial property. Yet it is also revealed from the study of the present invention that hexamine, when prepared in basic condition, is still capable of demonstrating an antibacterial effect. In addition, hexamine itself is a weak base and is found in the present study as being able to neutralize a number of odoriferous, volatile organic acids commonly formed from the bacterial decomposition of organic matter in the sweat. Furthermore, the hexamine comprising composition of the present invention demonstrates inhibition to aminoacylase enzymatic reaction, which is reported to be the mechanism by which organic matter in sweat is decomposed by bacteria which causes body odor. Lastly, formaldehyde released from hexamine is known to form keratin plugs at distal sweat ducts, which substantially block the opening of hair follicles and thus result in a significant reduction or suppression in sweat release. Accordingly, hexamine is found to play a multifunctional role in reducing or inhibiting the development of malodor in a deodorant composition and/or preparation.

Nevertheless, hexamine comprising deodorant preparations have also been reported to cause skin irritation. One possible cause of the skin irritation may relate to the release of formaldehyde, which is considered as a potential skin irritant and particularly, when the formaldehyde is present in high concentration such as in a highly acidic environment, in which the breakdown of hexamine to form formaldehyde as a by-product would be aggravated.

In the context of the present invention, the term "by-product" as used in relation to formaldehyde, or any aldehydes in general, does not preclude their possessing and/or exerting any functional characteristics. For example, in one embodiment of the present invention, the released formaldehyde from the decomposition of hexamine or hexane-comprising ingredient may serve as a subsidiary active to provide an additional or to support the deodorizing effect along with the hexamine or hexamine-comprising active ingredient, depending on the specific composition, preparation and application.

Accordingly, one embodiment of the present invention relates to a deodorizing composition for, for example, axilla application of a human subject. The composition comprises an active ingredient in an effective amount sufficient for reducing, inhibiting or suppressing any developed malodor caused by sweat at the body part. The active ingredient may comprise one or more of a hexamine, a derivative thereof and a compound thereof. The composition further comprises a buffer system for stabilizing the active ingredient, and thus, controlling or preventing release of any aldehydes such as formaldehyde as a result of hexamine decomposition. The buffer system adapted to maintain pH of the composition within a range of about 7.0 to about 11.0, and preferably, about 7.5 to about 10.0 after the composition is applied on the body part. The buffer system also provides a slightly basic to basic environment for neutralization of odoriferous organic acids resulting from the bacterial decomposition of organic compounds present in the sweat, which further assists in reducing any developed malodor.

In one embodiment, the buffer system may comprise one or more commonly known pH buffers adapted to provide the required buffer range as above described, such that the hexamine or hexamine comprising active ingredient in the composition can be substantially stabilized and that the effect of the acidic sweat can be substantially minimized. The buffer system may comprise one or more of an inorganic compound and an organic compound, such as but not limited to, one or more of 3-Morpholinopropane-1-sulfonic acid (MOPS), 4-(2-hydroxyethyl)-1-piperazineethanesulfonic acid) (HEPES), 3-(Cyclohexylamino)-1-propanesulfonic acid (CAPS), 3-[[1,3-dihydroxy-2-(hydroxymethyl)propan-2-yl]amino]-2-hydroxypropane-1-sulfonic acid (TAPS 0), 2-Amino-2-(hydroxymethyl)-1,3-propanediol (Trizma) and phosphate compound, as well as the salts thereof, or a combination thereof. Preferably, the buffer system may comprise an aqueous buffer solution to facilitate an aqueous formulation of the composition.

A number of embodied formulations and their corresponding compositions are provided in Table 1. For example, Formulations E, F, G, I, J (7.5) and J (6.2) are buffered, hexamine comprising composition in accordance with the present invention, while Formulations S and A are control experiments without having a buffer system in the composition.

TABLE 1

Formulations comprising hexamine as an deodorizing active ingredient: Formulation E, F, G, I, J (7.5) and J (6.2) are each prepared with a buffer system in accordance with an embodiment of the present invention, while Formulation S and A are prepared as control experiments, i.e. without the buffer system.

| Formulation | Composition (w/v %) | Formaldehyde (mM) at ambient condition |
|---|---|---|
| S (Control) | 40% Hexamine<br>3% Glycerol<br>1.27% Sodium bisulfite<br>0.55% Hydrochloric acid<br>Deionized water up to 100% | 40.90 ± 3.60 |
| A (Control) | 40% Hexamine<br>Deionized water up to 100% | 2.09 ± 0.07 |
| E | 35% Hexamine<br>5% ammonium carbonate<br>CAPS (200 mM) buffer solution (pH 10.8-11.0) up to 100% | 5.37 ± 0.71 |
| F | 40% Hexamine<br>3% Glycerol<br>CAPS (200 mM) buffer solution (pH 10.8-11.0) up to 100% | 1.57 ± 0.16 |
| G | 40% Hexamine<br>3% Glycerol<br>MOPS (200 mM) buffer solution (pH 7.7-7.9) up to 100% | 4.91 ± 0.47 |
| I | 40% Hexamine<br>5% ammonium carbonate<br>MOPS (200 mM) buffer solution (pH 7.7-7.9) up to 100% | 4.70 ± 0.52 |
| J (7.5) | 40% Hexamine<br>3% Glycerol<br>Sodium phosphate (200 mM) buffer solution (pH 7.4-7.6) up to 100% | 4.57 ± 0.32 |
| J (6.2) | 40% Hexamine<br>3% Glycerol<br>Sodium phosphate (200 mM) buffer solution (pH 6.0-6.2) up to 100% | 11.60 ± 1.30 |

The corresponding formaldehyde content after the formulation is applied on a test subject for 1 day has also been evaluated. Specifically, the formulations in which a buffer system has been introduced are found to demonstrate a significant reduction in the release of formaldehyde. For example, Formulation F demonstrated a release of less than 0.2% of formaldehyde (i.e. about 1.57 mM) at use, which is about 26 times less than when compared with the control Formulation S (i.e. about 40 mM of formaldehyde) under the same testing conditions. The significant reduction of formaldehyde has further been proven to reduce or prevent potential skin irritation. For example, the control Formulation S, which released a much higher concentration of formaldehyde, was found to cause skin irritation to the animal subject during a "Repeated Dermal Irritation Test" after 8 days of application, whereas no skin irritation was observed when using Formulation J (7.5), which released a much lower concentration of formaldehyde (i.e. about 4.57 mM) under the same testing conditions. Details of these studies are further elaborated in the experimental session.

Preferably, the active ingredient of the composition may comprise hexamine in about 5 w/v % to about 40 w/v % in respect of a total volume of the composition, and preferably, about 30 w/v % to about 40 w/v % such that the actives are to be provided in excess to ensure an effective concentration in the composition despite any possible decomposition or wash-off by sweat during practical uses.

The composition may optionally comprise one or more excipients, such as but not limited to, one or more humectants or emollients for topical application such as glycerol; antioxidants; pH adjustors such as hydrochloric acid and ammonium carbonate, etc. as shown in the formulations of Table 1. The composition may further comprise one or more additives for other purposes, such as but not limited to, cosmetic agents such as fragrances or essential oils; coloring agents; preservatives, thickening agents, stabilizers, propellants, solvents, fragrances, cooling agents, sun-blocking agents, etc. A person skilled in the art would understand that the composition of the present invention shall not be limited to any specific embodiments or exemplified formulations, but any additions, modifications or variations which are considered suitable or appropriate should also be encompassed.

Optionally, the composition may comprise one or more anti-bacterial agents and/or anti-fungal agents to further enhance the antiseptic effect, for example, disinfectants such as quaternary ammonium salts, or biocides such as chlorhexidine. The composition may also comprise one or more chelating agents such as ethylenediaminetetraacetic acid (EDTA) for inhibiting the aminoacylase enzymatic reaction of bacteria, which is known to generate odoriferous organic acids causing the malodor.

The present invention also relates to a deodorising preparation or a deodorant for use at a body part of a subject, comprising one or more of the above described embodiments of the composition. The deodorant is preferred to be topically applied or administered, and can be provided in one or more known forms of preparation, such as but not limited to, a solid, a gel, a cream, a powder, a liquid, a spray or a disposable wipe, i.e. a fabric or tissue paper impregnated with the composition in liquid form.

The present invention may further relate to a method of preparing a low or reduced skin-irritating composition for use in reducing, inhibiting or suppressing malodour from a body part of a subject. In one embodiment, the method comprises the step of providing an active ingredient in an effective amount, which may comprise one or more of hexamine, a derivative thereof and a compound thereof. The method further comprises providing a buffer system adapted to maintain pH of the composition within a range of about 7.0 to about 11.0, and preferably, about 7.5 to about 10.0 when the composition is applied on the body part. The buffer system is adapted to substantially neutralize topical acidity of the body part, including but not limited to, the acidity of natural sweat and/or the acidity caused by any volatile organic acids resulted from aminoacrylase enzymatic reaction during the bacterial decomposition of organic matters from sweat. The neutralization of topical acidity thus reduces or minimizes generation of skin-irritating by-products, for example, aldehydes or more specifically, formaldehyde from the hexamine comprising active ingredient.

EXPERIMENTAL

Preparation of the Embodied Formulations of the Composition

The following examples illustrate exemplified methods or processes for preparing the embodied formulations of the compositions, including Formulation S, A, E, F, G, I, J (7.5) and J (6.2), as shown in Table 1 above.

Formulation S in 10 mL:

4 g of hexamine, 0.3 mL of glycerol and 0.127 g of sodium bisulfite were added to a 20 ml container. Deionized water was added to the container and the solution was stirred. 0.055 mL of hydrochloric acid was added to the solution to form Formulation S in a volume of 10 mL.

Formulation A in 10 mL:

4 g of hexamine was added to a 20 mL container. Deionized water was added to form Formulation A in a volume of 10 mL.

Formulation E in 10 mL:

CAPS buffer solution (200 mM) was firstly prepared by dissolving 4.43 g of CAPS powder into 100 mL of deionized water or milli-Q water. The solution was then adjusted to pH 10.8-11.0 by the addition of sodium hydroxide solution or hydrochloric acid solution.

3.5 g of hexamine and 0.5 g of ammonium carbonate were added to a 20 mL container. The pH adjusted CAPS (200 mM) buffer solution was then added to the container to form Formulation E in a volume of 10 mL.

Formulation F in 10 mL:

CAPS buffer solution (200 mM) was firstly prepared by dissolving 4.43 g of CAPS powder into 100 mL deionized water or milli-Q water. The solution was then adjusted to pH 10.8-11.0 by the addition of sodium hydroxide solution or hydrochloric acid solution.

4 g of hexamine and 0.3 mL of glycerol were added to a 20 mL container. The pH adjusted CAPS (200 mM) buffer solution was added to the container to form Formulation F in a volume of 10 mL.

Formulation G in 10 mL:

MOPS buffer solution (200 mM) was firstly prepared by dissolving 4.19 g of MOPS powder into 100 mL deionized water or milli-Q water. The solution was then adjusted to pH 7.7-7.9 by the addition of sodium hydroxide solution or hydrochloric acid solution.

4 g of hexamine and 0.3 mL of glycerol were added to a 20 mL container. The pH adjusted MOPS (200 mM) buffer solution was added to the container to form Formulation G in a volume of 10 mL.

Formulation I in 10 mL:

MOPS buffer solution (200 mM) was firstly prepared by dissolving 4.19 g of MOPS powder into 100 mL deionized water or milli-Q water. The solution was then adjusted to pH 7.7-7.9 by the addition of sodium hydroxide solution or hydrochloric acid solution.

4 g of hexamine and 0.5 g of ammonium carbonate were added to a 20 mL container. The pH adjusted MOPS (200 mM) buffer solution was added to the container to form Formulation I in a volume of 10 mL.

Formulation J (7.5) in 10 mL:

Sodium phosphate buffer solution (200 mM) was firstly prepared by dissolving 1.2 g of sodium dihydrogen phosphate powder and 1.4 g of disodium hydrogen phosphate powder into 100 mL deionized water or milli-Q water. The solution was then adjusted to pH 7.4-7.6 by the addition of sodium hydroxide solution or hydrochloric acid solution.

4 g of hexamine and 0.3 mL of glycerol were added to a 20 mL container. The pH adjusted sodium phosphate (200 mM) buffer solution was added to the container to form Formulation J (7.5) in a volume of 10 mL.

Formulation J (6.2) in 10 mL:

Sodium phosphate buffer solution (200 mM) was firstly prepared by dissolving 1.2 g of sodium dihydrogen phosphate powder and 1.4 g of disodium hydrogen phosphate powder into 100 mL deionized water or milli-Q water. The solution was then adjusted to pH 6.0-6.2 by the addition of sodium hydroxide solution or hydrochloric acid solution.

4 g of hexamine and 0.3 mL of glycerol were added to a 20 mL container. The pH adjusted sodium phosphate (200 mM) buffer solution was then added to the container to form Formulation J (6.2) in a volume of 10 mL.

Formulation J (6.2) in 2000 mL:

Sodium phosphate buffer solution (200 mM) was firstly prepared by dissolving 24 g of sodium dihydrogen phosphate powder and 28 g of disodium hydrogen phosphate powder into 2000 mL deionized water or milli-Q water. The solution was then adjusted to pH 6.0-6.2 by the addition of sodium hydroxide solution or hydrochloric acid solution. 800 g of hexamine and 60 mL of glycerol were added to a 5 L container. The pH adjusted sodium phosphate (200 mM) buffer solution was added to the container to form Formulation J (6.2) in a volume of 2 L.

Acid Resistance

Acid resistance of the prepared formulations have been tested in synthesized, ISO sweat at various pHs and sweat volume.

Acid Resistance Test Under Different pH

Formulations S, A, F, G and J (7.5) were separately mixed with a synthesized, ISO sweat (sodium chloride 0.5%, L-histidine 0.05%, sodium dihydrogen phosphate 0.22%, pH adjusted with hydrochloric acid solution or sodium hydroxide solution) at different pH in 1:1 volume ratio. Each sample mixture was incubated for 3 hours followed by the detection of the released formaldehyde by Purpald Assay. Results from the Assay are shown in Table 2 below.

TABLE 2

Formaldehyde content in Formulations S, A, F, G and J (7.5) after being incubated in ISO sweat at different pHs.

| | Formaldehyde concentration [mM] | | | | |
|---|---|---|---|---|---|
| | S | A | F | G | J(7.5) |
| $[HCHO]_{initial}$ | 20.6 ± 1.1 | 0.38 ± 0.07 | 0.69 ± 0.12 | 2.51 ± 0.13 | 1.22 ± 0.36 |
| pH 4 | 25.8 ± 0.9 | 1.37 ± 0.04 | <LOQ | 2.24 ± 0.13 | 1.08 ± 0.08 |
| pH 4.5 | 26.5 ± 1.8 | 1.30 ± 0.11 | <LOQ | 2.28 ± 0.12 | 0.96 ± 0.13 |
| pH 5 | 26.4 ± 1.8 | 1.24 ± 0.08 | <LOQ | 2.29 ± 0.07 | 0.96 ± 0.05 |
| pH 5.5 | 25.7 ± 1.2 | 1.18 ± 0.10 | <LOQ | 2.22 ± 0.07 | 0.95 ± 0.16 |

TABLE 2-continued

Formaldehyde content in Formulations S, A, F, G and J (7.5)
after being incubated in ISO sweat at different pHs.

| | Formaldehyde concentration [mM] | | | | |
|---|---|---|---|---|---|
| | S | A | F | G | J(7.5) |
| pH 6 | 24.3 ± 0.3 | 1.07 ± 0.04 | <LOQ | 2.20 ± 0.10 | 1.28 ± 0.40 |
| pH 6.5 | 24.8 ± 0.9 | 0.88 ± 0.08 | <LOQ | 2.20 ± 0.11 | 0.95 ± 0.18 |
| pH 7 | 24.7 ± 0.6 | 0.70 ± 0.12 | <LOQ | 2.26 ± 0.05 | 0.90 ± 0.11 |
| pH 7.5 | 24.00 ± 0.03 | 0.61 ± 0.13 | <LOQ | 2.24 ± 0.09 | 1.00 ± 0.07 |
| pH 9 | 22.6 ± 2.2 | 0.46 ± 0.15 | <LOQ | 2.05 ± 0.12 | 0.82 ± 0.15 |

([HCHO]$_{initial}$ stands for "initial formaldehyde concentration"; LOQ stands for "limited of quantitation")

The study revealed that no significant increase of formaldehyde content was found in the embodied Formulations of F, G and J (7.5) comprising the buffer system even after the incubation with acidic sweat, such as at pH 4; whereas a significant increase of about 260% in formaldehyde content was observed in the control, Formulation A.

Acid Resistance Test Under Different Volume

In order to evaluate the acid resistant performance of the embodied composition in the presence of an excessive sweat, Formulations S, A, F, G and J (7.5) were separately mixed with an acidic ISO sweat at pH 4 in different volume ratios. Each sample mixture was incubated for 3 hours followed by the detection of the released formaldehyde by Purpald Assay. Controls have been prepared by mixing and incubating the tested Formulations with deionized water, and the experiments were conducted in parallel. Results from the Assay are shown in Table 3 below.

TABLE 3

Formaldehyde content in Formulations S, A, F, G
and J (7.5) after being incubated in acidic ISO
sweat at pH 4 in different volume percentages.

| Formulations | % of formulations in acidic sweat | [HCHO] in acidic sweat | [HCHO] in water |
|---|---|---|---|
| S | 75% | 24.20 ± 1.34 | 24.53 ± 0.93 |
| | 66.6% | 21.73 ± 0.84 | 22.08 ± 0.78 |
| | 50% | 20.68 ± 0.97 | 20.89 ± 1.01 |
| | 33.3% | 17.44 ± 1.44 | 17.07 ± 1.72 |
| | 25% | 14.47 ± 1.64 | 14.11 ± 1.16 |
| A | 75% | 1.22 ± 0.07 | 1.03 ± 0.07 |
| | 66.6% | 1.26 ± 0.08 | 0.91 ± 0.07 |
| | 50% | 1.42 ± 0.14 | 0.70 ± 0.05 |
| | 33.3% | 1.67 ± 0.19 | 0.49 ± 0.06 |
| | 25% | 2.18 ± 0.38 | 0.39 ± 0.06 |
| F | 75% | 0.03 ± 0.07 | 0.88 ± 0.08 |
| | 66.6% | 0.20 ± 0.06 | 0.76 ± 0.09 |
| | 50% | 0.12 ± 0.06 | 0.54 ± 0.11 |
| | 33.3% | 0.10 ± 0.06 | 0.31 ± 0.11 |
| | 25% | 0.11 ± 0.04 | 0.22 ± 0.12 |
| G | 75% | 2.66 ± 0.39 | 3.03 ± 0.36 |
| | 66.6% | 2.25 ± 0.35 | 2.64 ± 0.34 |
| | 50% | 1.68 ± 0.26 | 1.96 ± 0.28 |
| | 33.3% | 1.36 ± 0.17 | 1.31 ± 0.21 |
| | 25% | 1.19 ± 0.07 | 0.96 ± 0.16 |
| J (7.5) | 75% | 2.32 ± 0.10 | 2.99 ± 0.09 |
| | 66.6% | 1.91 ± 0.11 | 2.61 ± 0.09 |
| | 50% | 1.33 ± 0.07 | 2.04 ± 0.13 |
| | 33.3% | 1.14 ± 0.02 | 1.37 ± 0.01 |
| | 25% | 1.12 ± 0.04 | 1.07 ± 0.03 |

([HCHO] stands for "formaldehyde concentration")

In the test by mixing 25% of the non-buffered Formulation A in acidic sweat (i.e. 75% of acidic sweat), the mixture has demonstrated an increase of more than 400% in formaldehyde content when compared with the corresponding control experiment incubated in water; whereas the buffered formulations of the present invention such as Formulation J showed no significant change in the formaldehyde content under the same testing condition.

Skin Irritation

Formulations S and J (7.5) were further studied in a number of standard testing methods for skin irritation which are conducted under the required international standards and conditions. The testing methods include:

1) Repeated Dermal Irritation Test on rabbit subjects (Test method 1: Safety and Technical Standards for Cosmetics 2015 Chapter Six, 4 Dermal Irritation/Corrosion Test; and Test method 2: ISO 10993-10:2010, Biological evaluation of medical devices—Part 10: Tests for Irritation and Skin Sensitization);

2) Skin Sensitization Test on guinea pig subjects (Test method 1: Safety and Technical Standards for Cosmetics 2015 Chapter Six, 6 Skin Sensitization Test; and Test method 2: ISO 10993-10:2010, Biological evaluation of medical devices—Part 10: Tests for Irritation and Skin Sensitization);

3) Human Skin Patch Test (Test method 1: Safety and Technical Standards for Cosmetics, Ministry of Health, PRC, 2015 Edition; Test method 2: COLIPA (Walker A. P. et al: Test Guidelines for Assessment of Skin Compatibility of Cosmetic Finished Products in Man. Food and Chemical Toxicology 34, 1996, 651-660)).

Results summary of the tests are shown in Table 4 below.

TABLE 4

Results summary of the skin irritation tests.

| | Formulation S | Formulation J (7.5) |
|---|---|---|
| Repeated Dermal Irritation Test | | |
| Test 1 | Erythema developed on Day 8 | No visible irritation after 14 days |
| Test 2 | No visible irritation | No visible irritation |
| Skin Sensitization Test | | |
| Test 1 | No visible irritation | No visible irritation |
| Test 2 | No visible irritation | No visible irritation |
| Human Skin Patch Test | | |
| Test 1 | No visible irritation | No visible irritation |
| Test 2 | No visible irritation | No visible irritation |

Formulation J (7.5) of the present invention was demonstrated to cause no irritation in all of the above tests conducted under the standardized testing criteria. Particularly, Formulation J (7.5) was shown to cause no irritation to the rabbit subjects in the "Repeated Dermal Irritation Test"

after application continuously for 14 days on the skin of the subject; whereas for the non-buffered Formulation S, erythema was observed from Day 8 and until the end of the study at Day 14.

Enzymatic Inhibition

As earlier described, aminoacylase enzymatic reaction by bacteria is reported as one possible mechanism which causes sweat related malodor in human body. Particularly, the development of malodour is due to the presence of volatile organic acids generated as a bacterial decomposition byproduct from organic matters such as proteins in human sweat through the aminoacylase enzymatic reaction. In the study of the present invention, it is found that this enzymatic reaction requires magnesium cation as an essential co-factor, and the presence of hexamine would potentially compete with the relevant enzyme for magnesium cation through chelation. Accordingly, similar to the use of chelators such as EDTA for an anti-bacterial effect, the aminoacylase enzymatic activity would be substantially slowed down or even inhibited in the presence of hexamine.

This is further confirmed by the inhibition effect on *Corynebacterium Striatum* $N_\alpha$-acyl-glutamine aminoacylase by Formulation J (7.5) of the present invention, in which the enzymatic activity was found to reduce by 39-51%. The result demonstrated that, in addition to the known antiseptic properties, hexamine also plays a role in inhibiting the odor causing enzymatic reaction which reduces or removes the malodor.

Antibacterial Capability

The antibacterial capabilities of Formulations S, A, G and J (7.5) were evaluated. The formulations were separately incubated with the respective one of the tested bacteria: *Corynebacterium Striatum, Corynebacterium Diphtheria* and *Staphylococcus Epidermidis*, which were reported to cause human axillary odour. The respective minimum inhibitory concentration (MIC) and minimum bactericidal concentration (MBC) (in % of hexamine) were tabulated in Table 5.

TABLE 5

Antibacterial capabilities of Formulations S, A, G and J (7.5).

| Bacteria (Bacteria working stock: $5 \times 10^5$ to $1 \times 10^6$ cfu/ml) | Samples | | | |
| --- | --- | --- | --- | --- |
| | S | A | G | J (7.5) |
| Corynebacterium Striatum | MIC 0.65% MBC 0.65% | MIC 1.28% MBC 1.28% | MIC 2.55% MBC 2.55% | MIC 0.65% MBC 0.65% |
| Corynebacterium Diphtheria | MIC 1.25% MBC 2.5% | — | — | MIC 1.25% MBC 2.5% |
| Staphylococcus Epidermidis | MIC 0.31% MBC 1.25% | — | — | MIC 0.31% MBC 1.25% |

All hexamine containing formulations have demonstrated anti-bacterial effect to *Corynebacterium Striatum*, while Formulation J (7.5) showed the most pronounced effect among the four tested samples with anti-bacterial effect against all three of the bacteria tested.

Neutralization of Odoriferous Acid

Figure 2:
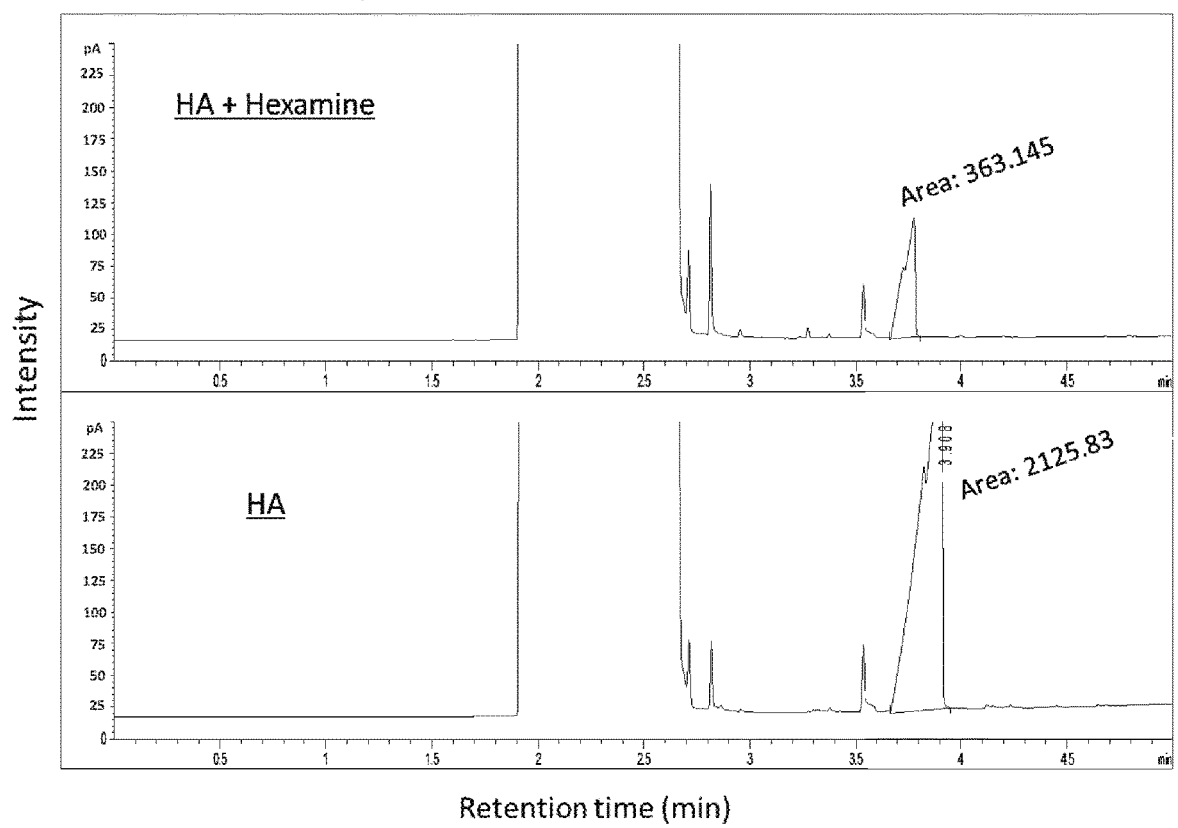
FIG. 2 is a GC-FID chromatogram showing neutralization of hexanoic acid by hexamine.

Hexamine, which is weakly basic in nature, was incubated with two commonly known odoriferous acids, i.e., 3-hydroxy-3-methyl-hexanoic acid (HMHA) and hexanoic acid, and the potential neutralization effect was studied by using a Gas Chromatograph with a Flame Ionization Detector (GC-FID). The chromatograms showing the neutralization of 3-hydroxy-3-methyl-hexanoic acid (HMHA) by sodium hydroxide and hexamine; and the neutralization of hexanoic acid by hexamine are shown in FIGS. 1 and 2, respectively. The results confirmed that hexamine is capable of neutralizing the tested odoriferous acids.

In summary, the present invention provides a novel composition for reducing, inhibiting or suppressing unpleasant odor such as sweat relating malodor developed from a body part of a subject. Particularly, the invention provides a low or reduced skin irritating, hexamine comprising composition for use in a deodorant preparation which demonstrates high potency in reducing, inhibiting or suppressing development of sweat relating malodor via a multifunctional deodorizing mechanism. The beneficial, low skin irritating effect is provided by the included buffer system in the composition which substantially stabilize hexamine in acidic sweat. The buffer system significantly reduces the break down and the subsequent release of formaldehyde from hexamine, which are known to be a skin-irritating agent. The buffer system also provides a subsidiary neutralization effect to any odoriferous acids results from the bacterial decomposition of organic matters in sweat, which further assists in reducing or preventing the development of malodor.

The present description illustrates the principles of the present invention. It will thus be appreciated that those skilled in the art will be able to devise various arrangements that, although not explicitly described or shown herein, embody the principles of the invention and are included within its spirit and scope.

Moreover, all statements herein reciting principles, aspects, and embodiments of the invention, as well as specific examples thereof, are intended to encompass both structural, compositional and functional equivalents thereof. Additionally, it is intended that such equivalents include both currently known equivalents as well as equivalents developed in the future, i.e., any elements developed that perform the same function, regardless of structure.

While the invention has been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

In the claims hereof, any element expressed as a means for performing a specified function is intended to encompass any way of performing that function. The invention as defined by such claims resides in the fact that the functionalities provided by the various recited means are combined and brought together in the manner which the claims call for. It is thus regarded that any means that can provide those functionalities are equivalent to those shown herein.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art.

The invention claimed is:

1. A low skin irritating composition for reducing, inhibiting or suppressing malodour developed from a body part of a subject, comprising:
    hexamine as an active ingredient in 20 w/v % to 40 w/v % in respect of a total volume of the composition; and
        a buffer system adapted to maintain pH of the composition within a range of about 7.0 to about 11.0 when the composition is applied on the body part;
        wherein the buffer system is adapted to substantially neutralise topical acidity of the body part thereby reducing or minimising generation of skin-irritating by-product from the active ingredient.

2. The low skin irritating composition according to claim 1, wherein the range of pH is of about 7.5 to about 10.0.

3. The low skin irritating composition according to claim 1, wherein the buffer system comprises one or more of an inorganic compound and an organic compound.

4. The low skin irritating composition according to claim 1, wherein the buffer system comprises one or more compounds selected from a group consisting of: 3-Morpholinopropane-1-sulfonic acid (MOPS), 4-(2-hydroxyethyl)-1-piperazineethanesulfonic acid) (HEPES), 3-(Cyclohexylamino)-1-propanesulfonic acid (CAPS), 3-[[1,3-dihydroxy-2-(hydroxymethyl)propan-2-yl]amino]-2-hydroxypropane-1-sulfonic acid (TAPSO), 2-Amino-2-(hydroxymethyl)-1,3-propanediol (Trizma) and a phosphate; a salt thereof; and a combination thereof.

5. The low skin irritating composition according to claim 1, wherein the buffer system comprises an aqueous buffer solution.

6. The low skin irritating composition according to claim 1, further comprising one or more excipients selected from a group consisting of: glycerol, sodium bisulfite, hydrochloric acid, ammonium carbonate.

7. The low skin irritating composition according to claim 1, further comprising one or more of an anti-bacterial agent and an anti-fungal agent.

8. The low skin irritating composition according to claim 7, wherein the anti-bacterial agent comprises one or more of a disinfectant and a biocide.

9. The low skin irritating composition according to claim 1, further comprising a chelating agent.

10. The low skin irritating composition according to claim 1, further comprising one or more additives selected from a group consisting of a cosmetic agent, a preservative, a thickening agent, a stabilizer, a pH adjuster, a propellant, a solvent, a fragrance, a cooling agent, a sun-blocking agent.

11. A deodorising preparation for use at a body part of a subject, comprising a low skin irritating composition for reducing, inhibiting or suppressing malodour developed from a body part of a subject, comprising:
    hexamine as an active ingredient in 20 w/v % to 40 w/v % in respect of a total volume of the composition; and
        a buffer system adapted to maintain pH of the composition within a range of about 7.0 to about 11.0 when the composition is applied on the body part;
        wherein the buffer system is adapted to substantially neutralise topical acidity of the body part thereby reducing or minimising generation of skin-irritating by-product from the active ingredient.

12. The deodorising preparation according to claim 11, wherein the preparation is provided in one or more of the following forms: a solid, a gel, a cream, a powder, a liquid, a spray and a wipe.

13. The deodorising preparation according to claim 11, wherein the preparation is to be topically administered.

* * * * *